United States Patent [19]
Warren

[11] Patent Number: 6,090,784
[45] Date of Patent: Jul. 18, 2000

[54] RNA POLYMERASE II PEPTIDES AND METHODS OF USE

[75] Inventor: Stephen L. Warren, Orange, Conn.

[73] Assignee: Yale University, New Haven, Conn.

[21] Appl. No.: 08/566,190

[22] Filed: Dec. 1, 1995

[51] Int. Cl.[7] .......................... A61K 38/00; A61K 38/04; A01N 37/18; C12N 9/12
[52] U.S. Cl. .................................. 514/16; 514/2; 514/12; 514/17; 435/194; 530/329; 530/402
[58] Field of Search ............................ 435/194; 530/329, 530/402; 514/2, 12, 44, 16, 17; 536/23.4

[56] References Cited

U.S. PATENT DOCUMENTS

| | | |
|---|---|---|
| 4,244,946 | 1/1981 | Rivier et al. . |
| 4,305,872 | 12/1981 | Johnston et al. . |
| 4,316,891 | 2/1982 | Guillemin et al. . |
| 4,629,784 | 12/1986 | Stammer . |
| 4,792,525 | 12/1988 | Ruoslahti et al. . |
| 5,565,327 | 10/1996 | Greenleaf et al. .......................... 435/21 |

FOREIGN PATENT DOCUMENTS

| | | |
|---|---|---|
| WO 93/17102 | 9/1993 | WIPO . |
| WO 95/26136 | 10/1995 | WIPO . |
| WO 96/17074 | 6/1996 | WIPO . |

OTHER PUBLICATIONS

Allison et al., *Mol. Cell. Biol.*, Jan. 1988, 8(1): 321–329.
Allison et al., *Cell*, vol. 42: 599–610, 1985.
Agrawal, et al., "Drug Disposition—Pharmocokinetics of Antisense Oligonucleotides," *Clin. Pharmacokinetics* 28, 7–16 (1995).
Agrawal and Akhtar, "Advances in Antisense Efficacy and Delivery," *Trends in Biotechnol.*, 13, 197–199 (1995).
Agrawal, et al., "Modified Oligonucleotides as Therapeutic and Diagnostic Agents," *Current Opinion in Biotechnol.* 6(1), 12–19 (1995).
Ahearn et al., "Cloning and Sequence Analysis of the Mouse Genomic Locus Encoding the Largest Subunit of RNA Polymerase, II," *J. Biol. Chem.* 262, 10695–10705 (1987).
Akoulitchev, et al., "Requirement for TFIIH Kinase Activity in Transcription by RNA Polymerase, II," *Nature* 377, 557–660 (1995).
Allison, et al., "The C–Terminal Domain of the Largest Subunit of RNA Polymerase II of Saccharomyces Cervisiae, Drosophila Melanogaster, and Mamals: A Conserved Structure with an Essential Function," *Molecular and Cellular Biology*, 8(1), 321–329 (1988).
Altman, et al., "Recent Studies of Ribonuclease P," *Faseb J.* 7(1), 7–14 (1993).
Altman, "Commentary—RNA Enzyme–Directed Gene Therapy," *Proc. Natl. Acad. Sci. USA* 90(23), 10898–10900 (1993).
Barinaga, "Ribozymes: Killing the Messenger," *Science* 262, 1512–1514 (1993).
Baron, Andre et al., "Localization of the Centrin–Related 165,000–$M_1$ Protein of $PtK_2$ Cells During the Cell Cycle," *Cell Motil. and the Cytoskel.* 18, 1–14 (1991).

Bartolomei et al, "Genetic Analysis of the Repetitive Carboxyl–Terminal Domain of the Largest Subunit of Mouse RNA Polymerase II," *Mol. Cell. Biol.*, 8, 330–339 (1988).
Biggs et al., "Structure of the Eukaryotic Transcription Apparatus: Features of the Gene for the Largest Subunit of Drosophila RNA Polymerase II," *Cell* 42, 611–621 (1985).
Bird and Riddle, "Molecular Cloning and Sequencing of ama–I, the Gene Encoding the Largest Subunit of *Caenorhabditis elegans* RNA Polymerase II," *Mol. Cell. Biol.* 9, 4119–4130 (1989).
Corden et al., "A Unique Structure at the Carboxyl Terminus of the Largest Subunit of Eukaryotic RNA Polymerase II," *Proc. Natl. Acad. Sci. USA* 82, 7934–7938 (1985).
Crooke, "Oligonucleotide Therapeutics: A Prospectus," *Antisense Res. Develop.* 3, 1–2 (1993).
Crystal, "Transfer of Genes to Humans: Early Lessons and Obstacles to Success," *Science* 270, 404–410 (1995).
De Clercq, "Antiviral Therapy for Human Immonodeficiency Virus Infections," *Clin. Microbiol. Rev.* 8, 200–239 (1995).
Dietrich et al., "Analysis of the Genes Encoding the Largest Subunit of RNA Polymerase II in Arabidopsis and Soybean," *Plant Mol. Biol.* 15, 207–223 (1990).
Evers et al., "Trypanosoma Brucei Contains Two RNA Polylmerase II Largest Subunit Genes with an Altered C–Terminal Domain," *Cell* 56, 585–597 (1989).
Feaver et al, "Relationship of CDK–Activating Kinase and RNA Polymerase II CTD Kinase TFIIH/TFIIK," *Cell* 79, 1103–1109 (1994).
Harding, "NMR Studies YSPTSPSY: Implications for the Design of DNA Bisintercalators," *Journal of Medicicnal Chemistry*, 35, 4658–4664 (1992).
Herrmann, "Cancer Gene Therapy: Principles, Problems, and Perspectives," *J. Molec. Med.* 73, 157–163 (1995).

(List continued on next page.)

*Primary Examiner*—Robert A. Wax
*Assistant Examiner*—Einar Stole
*Attorney, Agent, or Firm*—Arnall Golden & Gregory, LLP

[57] ABSTRACT

A macromolecular delivery method that utilizes a series of peptides with unique and versatile nuclear targeting properties has been developed, where the peptides are derived from the COOH terminal domain (CTD) of the largest subunit of RNA polymerase II and include heptapeptide units similar or identical to the following consensus sequence: Tyrosine—Serine—Proline—Threonine—Serine—Proline—Serine $(YSPTSPS)_x$ (SEQ ID NO. 1). When expressed in vivo, the CTD peptides are phosphorylated and they accumulate in discrete compartments within the nucleus. The CTD peptides concentrate indicator molecules in discrete subnuclear compartments where pre-mRNA molecules are synthesized and spliced. The length and composition of the CTD peptides can be manipulated to obtain different intranuclear partitioning properties. The CTD peptides are functional in the nuclei of *S. cerevisiae, S. pombe*, nematodes, insects, plants, and all vertebrates. Since the CTD peptides accumulate precisely in discrete sites inhabited by RNA polymerase II and the spliceosomes, they should be useful in genetic therapy technologies.

26 Claims, 5 Drawing Sheets

OTHER PUBLICATIONS

Jokerst et al., "Analysis of the Gene Encoding the Largest Subunit of RNA Polymerase II in Drosophila," *Mol. Gen. Genet.* 215, 266–275 (1989).

Khiat, et al., "Structural Differences Between the Free and Bound States of DNA–Bisintercalating Peptide YSPTSPSY," *Journal of Medicinal Chemistry*, 39(21), pp. 2492–2498 (1996).

Koleske, et al., "The RNA Polymerase II Holoenzyme and Its Implications for Gene Regulation," *Trends in Biochemical Sciences*, 20, 113–116 (1995).

Liu and Altman, "Inhibition of Viral Gene Expression by the Catalytic RNA Subunit of RNase P from *Escherichia coli*," *Genes & Devel.* 9(4), 471–480 (1995).

Merrifield J., "Solid Phase Peptide Synthesis. I. The Synthesis of a Tetrapeptide," *J. Am. Chem. Soc.* 85, 2149–2154 (1964).

Miller, "Human Gene Therapy Comes with Age," *Nature* 357, 455–460 (1992).

Mulligan, "The Basic Science of Gene Therapy," *Science* 260, 926–932 (1993).

Price and Pettijohn, "Redistribution of the Nuclear Mitotic Apparatus Protein (NuMA) during Mitosis and Nuclear Assembly—Properties of Purified NuMA Protein," *Exp. Cell Res.* 166, 295–311 (1986).

Roy et al, "The MO15 Cell Cycle Kinase is Associated with the TFIIH Transcription–DNA Repair Factor," *Cell* 79, 1093–1101 (1994).

Sambrook, Frisch & Maniatis, *Molecular Cloning: A Laboratory Manual*, 2nd Ed., (Cold Spring Harbor Laboratory, NY 1989), "Table of Contents."

Seipel, et al., "Basal Components of the Transcription Apparatus (RNA Polymerase II, TATA–binding Protein) Contain Activation Domains: Is Repetitive C–Terminal Domain (CTD) of RNA Polymerase II a Portable Enhancer Domain?," *Chemical Abstracts*, 122(17), Abstract No. 206769 (1944).

Sullenger and Cech, "Tethering Ribozymes to a Retroviral Packaging Signal for Destruction of Viral RNA," *Science* 262, 1566–1569 (1993).

Temsamani, et al., "Cellular Uptake of Oligodeoxynucleotide Phosphorothioates and Their Analogs," *Antisense Res. & Devel.* 4, 35–42 (1994).

Wagner, "Gene Inhibition Using Antisense Oligodeoxynucleotides," *Nature* 372, 333–335 (1994).

Warren, et al., "Coordinated Transcription–Dependent Redistribution," *Journal of Cellular Biochemistry*, Supplement 21B, p.141 (1995).

Warren and Nelson, "Nonmitogenic Morphoregulatory Action of $pp60^{v-src}$ on Multicellular Epithelial Structures," *Mol. Cell. Biol.* 7, 1326–1337 (1987).

Winzerith et al., "Complete Sequence of the Human RNA Polymerase II Largest Subunit," *Nucleic Acids Research* 20, 910 (1992).

Yang et al., "NuMA: An Unusually Long Coiled–Coil Related Protein in the Mammalian Nucleas," *J. Cell Biol.* 116, 1303–1317 (1992).

Yu, et al., "A Hairpin Ribozyme Inhibits Expression of Diverse Strains of Human Immuodeficiency Virus Type I," *Proc. Natl. Acad. Sci. USA* 90, 6340–6344 (1993).

Yuan, et al., "Targeted Cleavage of mRNA by Human RNase P," *Proc. Natl. Acad. Sci. USA* 89(17), 8006–8010 (1992).

Zamecnik, et al., "Oligodeoxynucleotide Hybridization Inhibition of HIV and Influenza Virus," *Nucleic Acids Symp. Series* 24, 127–131 (1991).

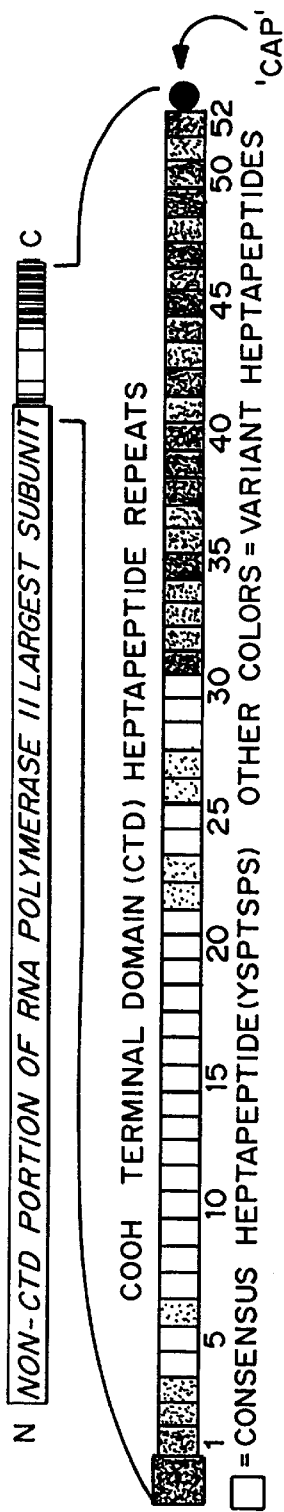
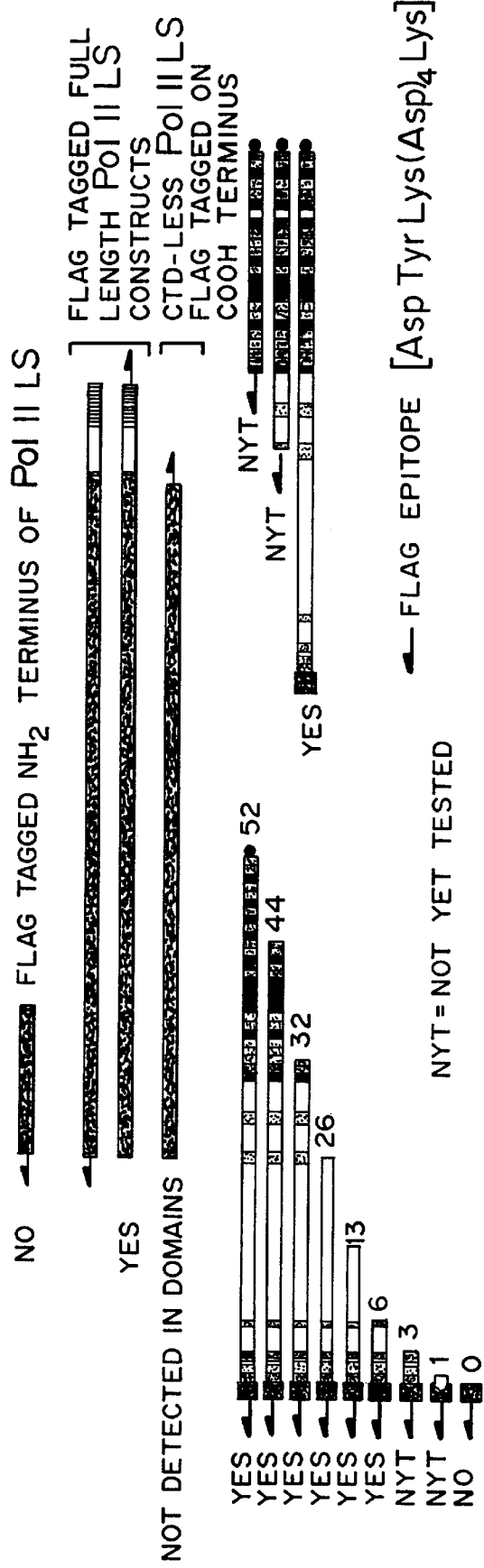
FIG. 2a
FIG. 2b

```
                          SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
         (A) LENGTH: 7 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:1:

Tyr Ser Pro Thr Ser Pro Ser
1               5

(2) INFORMATION FOR SEQ ID NO:2:

(i) SEQUENCE CHARACTERISTICS:
         (A) LENGTH: 7 amino acids
         (B) TYPE: amino acid
         (C) STRANDEDNESS: single
         (D) TOPOLOGY: linear (ii) MOLECULE TYPE: peptide
```

(xi) SEQUENCE DESCRIPTION: SEQ ID NO:2:

Tyr Ser Pro Thr Ser Pro Asn
1               5

(2) INFORMATION FOR SEQ ID NO:3:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:3:

Tyr Thr Pro Thr Ser Pro Asn
1               5

(2) INFORMATION FOR SEQ ID NO:4:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:4:

Tyr Ser Pro Thr Ser Pro Ala
1               5

(2) INFORMATION FOR SEQ ID NO:5:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:5:

Tyr Thr Pro Gln Ser Pro Ser
1               5

(2) INFORMATION FOR SEQ ID NO:6:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:6:

Tyr Glu Pro Arg Ser Pro Gly Gly
1               5

(2) INFORMATION FOR SEQ ID NO:7:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:7:

Tyr Ser Pro Thr Ser Pro Thr
1               5

(2) INFORMATION FOR SEQ ID NO:8:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:8:

Tyr Ser Pro Thr Ser Pro Lys
1               5

(2) INFORMATION FOR SEQ ID NO:9:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:9:

Tyr Thr Pro Thr Ser Pro Lys
1               5

(2) INFORMATION FOR SEQ ID NO:10:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:10:

Tyr Ser Pro Thr Thr Pro Lys
1               5

(2) INFORMATION FOR SEQ ID NO:11:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:11:

Tyr Ser Pro Thr Ser Pro Val
1               5

(2) INFORMATION FOR SEQ ID NO:12:

(i) SEQUENCE CHARACTERISTICS:
            (A) LENGTH: 7 amino acids
            (B) TYPE: amino acid
            (C) STRANDEDNESS: single
            (D) TOPOLOGY: linear

```
        (ii) MOLECULE TYPE: peptide (xi) SEQUENCE DESCRIPTION: SEQ ID NO:12:

Tyr Ser Pro Thr Ser Pro Gly
1               5

(2) INFORMATION FOR SEQ ID NO:13:

(i) SEQUENCE CHARACTERISTICS:
             (A) LENGTH: 7 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:13:

Tyr Ser Leu Thr Ser Pro Ala
1               5

(2) INFORMATION FOR SEQ ID NO:14:

(i) SEQUENCE CHARACTERISTICS:
             (A) LENGTH: 7 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:14:

Tyr Thr Pro Ser Ser Pro Ser
1               5

(2) INFORMATION FOR SEQ ID NO:15:

(i) SEQUENCE CHARACTERISTICS:
             (A) LENGTH: 7 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:15:

Tyr Ser Pro Ser Ser Pro Ser
1               5

(2) INFORMATION FOR SEQ ID NO:16:

(i) SEQUENCE CHARACTERISTICS:
             (A) LENGTH: 7 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:16:

Tyr Thr Pro Thr Ser Pro Ser
1               5

(2) INFORMATION FOR SEQ ID NO:17:

(i) SEQUENCE CHARACTERISTICS:
             (A) LENGTH: 7 amino acids
             (B) TYPE: amino acid
             (C) STRANDEDNESS: single
```

```
            (D) TOPOLOGY: linear (ii) MOLECULE TYPE: peptide (xi) SEQUENCE DESCRIPTION: SEQ ID NO:17:

Tyr Ser Pro Ser Ser Pro Glu
1               5

(2) INFORMATION FOR SEQ ID NO:18:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

Tyr Thr Pro Gln Ser Pro Thr
1               5

(2) INFORMATION FOR SEQ ID NO:19:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

Tyr Ser Pro Ser Ser Pro Arg
1               5

(2) INFORMATION FOR SEQ ID NO:20:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

Asp Tyr Lys Asp Asp Asp Asp Lys
1               5

(2) INFORMATION FOR SEQ ID NO:21:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (B) LOCATION: 2,4,5,7
        (D) OTHER INFORMATION:  Xaa can be any amino acid.

(xi) SEQUENCE DESCRIPTION: SEQ ID NO:21:

Tyr Xaa Pro Xaa Xaa Pro Xaa
1               5

(2) INFORMATION FOR SEQ ID NO:22:
```

```
        (i) SEQUENCE CHARACTERISTICS:
            (A) LENGTH: 3 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:22:

Gly Ser Thr
1

(2) INFORMATION FOR SEQ ID NO:23:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:23:

Ile Ser Pro Asp Asp Ser Asp Glu Glu Asn
1               5                   10

(2) INFORMATION FOR SEQ ID NO:24:

(i) SEQUENCE CHARACTERISTICS:
            (A) LENGTH: 32 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:24:

Tyr Ser Pro Ala Trp Ser Pro Thr Pro Gly Ser Pro Gly Ser Pro Gly
1               5                   10                  15

Pro Ser Ser Pro Tyr Ile Pro Ser Pro Gly Gly Ala Met Ser Pro Ser
            20                  25                  30

(2) INFORMATION FOR SEQ ID NO:25:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:25:

Tyr Pro Ser Thr Ser Pro Ser
1               5
```

RNA POLYMERASE II PEPTIDES AND METHODS OF USE

The United States government has rights in this invention by virtue of National Cancer Institute Grant No. K08 CA01339 and March of Dimes Birth Defects Foundation Grant No. 5-91-0647.

BACKGROUND OF THE INVENTION

This relates to the fields of immunology and protein biochemistry and more particularly relates to RNA polymerase II peptides useful for nuclear targeting.

The notion that genes might be replaced or specifically inhibited seems realistic given the recent explosion in human genome research; the spectacular successes in transgenic animal technology; the development of viral and non-viral ex vivo gene transfer techniques; and the intermittent successes of antisense oligodeoxynucleotide and ribozyme technologies. The gene therapy concept has led to the formation of many biotech companies specializing in gene transfer, antisense oligonucleotides and catalytic RNAs. The pharmaceutical industry and the NIH have also made significant financial commitments to develop these technologies. Millions of dollars of investment capital and grant funds have been spent on gene therapy research, and several human gene therapy clinical trials are underway. Despite all of this excitement, genetic therapy is still in a very early stage of development. It is clear that some very difficult engineering problems must be overcome before gene transfer, antisense and catalytic RNA technologies will be used to treat human diseases.

Technical barriers can be divided into three categories: Reagent design: optimization of nucleic acid activity through gene transfer and antisense oligodeoxynucleotides and catalytic DNAs; Delivery: formulating and delivering nucleic acids into cells; and Targeting: ensuring that nucleic acid reagents are bioavailable after they enter the cell. Some of the issues that must be addressed in targeting and delivery include: a substantial fraction of the reagent (transgene/oligo/catalytic RNA) must enter the nucleus; intranuclear targeting of nucleic acid reagents must be optimized and intranuclear sequestration must be avoided; if stable expression is desired, transgenes must recombine with chromosomes; stable and transient transgenes must be accessible to the transcription machinery; and oligos and catalytic RNAs must gain access to their pre-mRNA targets.

Gene therapy research has emphasized reagent design and delivery, but not targeting. To tackle the problems of reagent design and delivery, the gene therapy researchers have drawn from a vast body of research on gene regulation, nucleic acid biochemistry, virology and membrane biology. Significant advances have been made in the understanding of genomic organization and chromatin structure; RNA polymerase II-mediated transcription; packaging and splicing of pre-mRNA; stability and translational efficiency of mRNA; kinetics and thermodynamics of nucleic acid hybridization; catalytic RNAs; viral 'vectorology' and liposome-mediated transfer of nucleic acids across cell membranes. Based upon this strong fund of knowledge, some of the problems associated with reagent design and delivery have been successfully addressed. The problem of targeting—i.e. concentrating the reagent in the appropriate subnuclear compartment—has received far less attention. One reason may be that reagent design and delivery are perceived as more tractable problems. It seems relatively straightforward to increase the Tm of an oligonucleotide; to optimize the composition of a liposome; or to modify the enhancer in a plasmid, changes which can be rapidly assessed in vitro. On the other hand, it seems difficult to manipulate or even to investigate the fate of plasmids, antisense oligos or catalytic RNAs after they cross the plasma cell membrane.

It is not known if nucleic acid reagents are bioavailable or sequestered once they enter the nucleus. Some nucleic acid reagents. for example, plasmids and oligonucleotides, accumulate in the nucleus without the help of a nuclear localization signal (NLS). This is usually considered a fortunate outcome, since the reagent has entered the desired subcellular compartment. Furthermore, it is tempting to think that nuclear accumulation indicates bioavailability. However, one cannot know how much of a nucleic acid reagent is bioavailable, and how much is sequestered inside the nucleus. To consider whether a nucleic acid reagent actually gains access to the desired subnuclear compartment, one should ask why transfected oligonucleotides typically accumulate in the nucleus. Like small peptides, oligos do not require a nuclear localization sequence (NLS) to enter the nucleus, since they can passively traverse nuclear pores. Presumably, oligos that diffuse into the nucleus are rapidly bound to intranuclear macromolecules, which retain them in this organelle. The nucleus contains a huge surplus of DNA and RNA binding proteins. The majority of nucleic acid binding proteins (e.g. hnRNPs and DNA binding proteins) are not associated with chromosomes at a given time, and therefore have the potential to bind RNA and/or DNA oligonucleotides. Indeed, the nucleus may be viewed as a high capacity chromatographic column, packed with nucleic acid binding proteins. Adventitious binding interactions with such proteins may severely inhibit the activities of antisense DNA oligos, catalytic RNAs and Plasmids may not be free to recombine with the chromosomes, or they may be sequestered from the RNA polymerase II transcriptional machinery. Ironically, therefore, the accumulation of a nucleic acid reagent in the nucleus may reflect its sequestration rather than its bioavailability.

To develop effective non-viral gene transfer and oligonucleotide-based therapies, it is important to realize that the nucleus is densely packed with chromosomal and extrachromosomal nucleoprotein complexes which exist in a relatively insoluble therapeutic agents can diffuse freely throughout this organelle. Indeed, large segments of pre-mRNA molecules are probably 'buried' within ribonucleoprotein complexes, so it may be very difficult for soluble oligonucleotides and ribozymes to gain access to their target nucleic acid sequences in vivo.

It is therefore an object of the present invention to provide a therapeutic tool for the delivery of therapeutic agents from the surface of a cell to the cell nucleus or from a cell receptor to a targeted gene, and in particular to target therapeutics to specific intranuclear regions of the cells where they are bioavailable.

SUMMARY OF THE INVENTION

A macromolecular delivery method that utilizes a series of peptides with unique and versatile nuclear targeting properties has been developed, where the peptides are derived from the COOH terminal domain (CTD) of the largest subunit of RNA polymerase II and include heptapeptide units similar or identical to the following consensus sequence: Tyrosine—Serine—Proline—Threonine—Serine—Proline—Serine (YSPTSPS)$_x$ (SEQ ID NO. 1).

When expressed in vivo, the CTD peptides are phosphorylated and they accumulate in discrete compartments within the nucleus. The CTD peptides concentrate indicator molecules in discrete subnuclear compartments where pre-mRNA molecules are synthesized and spliced. The length and composition of the CTD peptides can be manipulated to obtain different intranuclear partitioning properties. The CTD peptides are functional in the nuclei of *S. cerevisiae, S. pombe*, nematodes, insects, plants, and all vertebrates. Since the CTD peptides accumulate precisely in discrete sites inhabited by RNA polymerase II and the spliceosomes, they should be useful in genetic therapy technologies. CTD peptides can concentrate antisense oligonucleotides, catalytic RNAs and transgenes in the nuclear compartment where the pre-mRNAs are synthesized and processed. The CTD peptides should minimize intranuclear sequestration of therapeutic polynucleotides.

BRIEF DESCRIPTION OF THE DRAWINGS

In FIG. 1A, columns 1 through 6 are shown where column 1 is on the left, and column 6 is on the right. Column 1 shows: SEQ ID NO. 4; SEQ ID NO. 6; SEQ ID NO. 5; SEQ ID NO. 1; SEQ ID NO. 1; SEQ ID NO. 2; SEQ ID NO. 1; SEQ ID NO. 1; SEQ ID NO. 1; and, SEQ ID NO. 1, from top to bottom, respectively. Column 2 shows SEQ ID NO. 1 repeated ten times from top to bottom. Column 3 shows: SEQ ID NO. 1; SEQ ID NO. 2; SEQ ID NO. 2; SEQ ID NO. 1; SEQ ID NO. 1; SEQ ID NO. 1; SEQ ID NO. 2; SEQ ID NO. 1; SEQ ID NO. 1; and, SEQ ID NO. 1, from top to bottom, respectively. Column 4 shows: SEQ ID NO. 19; SEQ ID NO. 18; SEQ ID NO. 14; SEQ ID NO. 15; SEQ ID NO. 8; SEQ ID NO. 16; SEQ ID NO. 17; SEQ ID NO. 9; SEQ ID NO. 8; and, SEQ ID NO. 8, from top to bottom, respectively. Column 5 shows: SEQ ID NO. 7; SEQ ID NO. 10; SEQ ID NO. 7; SEQ ID NO. 11; SEQ ID NO. 8; SEQ ID NO. 7; SEQ ID NO. 8; SEQ ID NO. 7; SEQ ID NO. 8; SEQ ID NO. 22; and, SEQ ID NO. 12, from top to bottom, respectively. Column 6 shows: SEQ ID NO. 7; SEQ ID NO. 13; and, SEQ ID NO. 23, from top to bottom, respectively.

FIG. 2A is a schematic of Flag-tagged CTD peptides; FIG. 2B is a schematic of the ability of various proteins to target flag peptides to discrete nuclear domains. The flag epitope sequence shown is also set forth in SEQ ID NO. 20.

DETAILED DESCRIPTION OF THE INVENTION

Figure 1A:
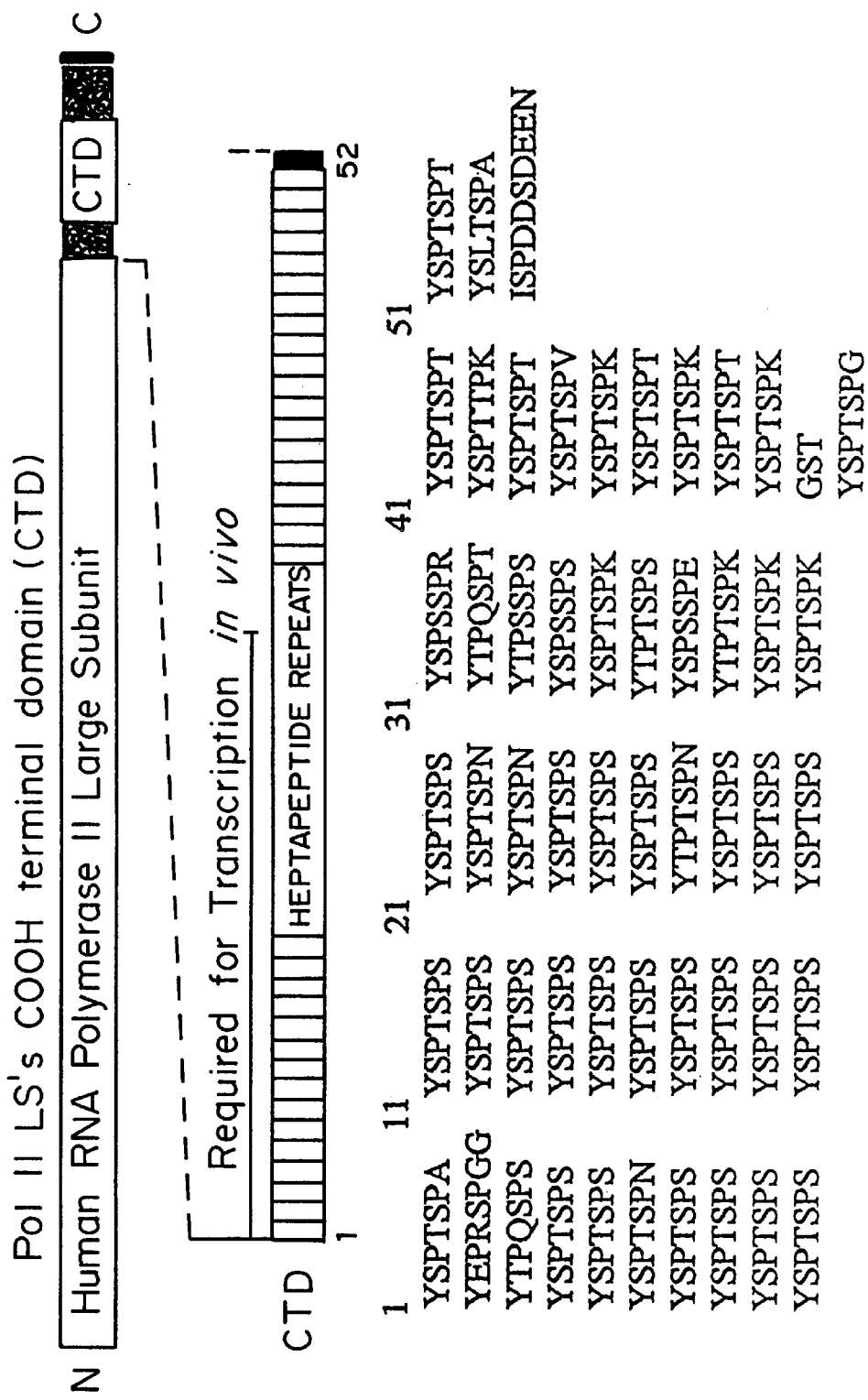
FIG. 1A is a schematic of the Pol II LS's COOH terminal domain (CTD)

Inside of the mammalian nucleus there are no bilayers or stable filamentous cytoskeletal structures of the type known in the cytoplasm, yet a vast number of biochemical processes take place within this extremely compact organelle: DNA replication and methylation; DNA repair; Polymerase II-mediated gene transcription; pre-mRNA splicing; pre-mRNA packaging and hnRNA export; Polymerase I-mediated transcription; rRNA processing and ribosome biogenesis; Polymerase III-mediated gene transcription and tRNA processing. In addition, many signal transduction pathways originating at the cell membrane converge on intranuclear targets. These diverse processes must be partially segregated or compartmentalized. Clearly each chromosome represents a 'compartment' within the nucleus, but at a given time the majority of intranuclear proteins and nucleic acids (i.e. RNA) are not bound to chromatin. It is becoming increasingly clear that many of these non-chromosomal proteins and nucleic acids are organized in discrete extrachromosomal compartments. Recent work from several labs has shown that various transcriptional proteins are neatly 'deposited' in solid phase extrachromosomal domains when they are not engaged in transcription. It has now been determined that unengaged RNA polymerase II (Pol II) is stored in domains that also harbor splicing complexes. As a result, it is possible to use peptides derived from RNA polymerase II as targeting molecules to extrachromosomal compartments.

The targeting molecules described herein are derived from the RNA polymerase II carboxyl terminus, consisting of a number of repeats, as described in more detail below.

I. RNA Polymerase II LS and Intracellular Role.

RNA polymerases

RNA polymerases are enzymes that synthesize cellular RNA from a DNA or RNA template. RNA synthesized by an RNA polymerase is complementary to its template. Cellular RNA polymerases take their instructions from DNA and are termed DNA-dependent polymerases. The polymerases of some viruses synthesize RNA according to the instructions given by RNA and are referred to as RNA-dependent polymerases. The nucleus of eukaryotes contains three types of RNA polymerases. RNA polymerase I is located in nucleoli and transcribes the genes for 18S, 5.8S, and 28S ribosomal RNA (rRNA). RNA polymerase II is located in the nucleoplasm and synthesizes the precursors of messenger RNA (mRNA) and several small RNA molecules. The splicing of mRNA precursors into mRNA molecules is performed by small nuclear ribonucleoprotein particles (snRNPs) in a spliceosome complex. RNA polymerase III is also located in the nucleoplasm and synthesizes the 5S rRNA molecule and the transfer RNA molecules (tRNA).

DNA-dependent RNA polymerase II is the enzyme that catalyzes pre-mRNA synthesis in all eukaryotic organisms. The large subunit of DNA-dependent RNA polymerase II (Pol II LS) has a molecular weight of between approximately 220 and 240 kDa, depending on the degree of phosphorylation. Pol II LS is highly conserved in eukaryotic cells from yeast to humans, as discussed below.

RNA polymerase II (Pol II) transcribes protein encoding genes in all eukaryotic cells, and has a highly conserved structure and subunit composition. The Pol II multimeric enzyme in all species from yeast to humans has 10±2 subunits. The largest subunit (Pol II LS, 240 kDa) and the second largest subunit (Pol II S2, 140 kDa) retain significant homology to the β and β' subunits of *E. coli* RNA polymerase, and contribute to the enzyme's catalytic core that directly contacts DNA.

Intracellular Location of Pol II LS

The location of Pol II LS in cells was determined by immunofluorescence microscopy using procedures described by Warren and Nelson, *Mol. Cell. Biol.* 7: 1326–1337 (1987), and the anti-Pol II LS antibodies described in U.S. Ser. No. 08/348,718, filed Dec. 2, 1994, the teachings of which are incorporated herein. Cells were grown on glass coverslips, and fixed in 1.7% paraformaldehyde (weight/volume) in phosphate buffered saline (PBS) containing 10 mM $Na_2HPO_4/NaH_2PO_4$, pH 7.2, and 150 mM NaCl. The fixed cells were washed in PBS for 15 minutes and permeabilized with PBS containing 0.5% TRITON X-100 surfactant and 2 mM $MgCl_2$ for 15 minutes at room temperature. Cells were incubated in monoclonal antibody H-5 (anti-Pol II LS) or control IgM (10 μg/ml) for 60 min at room temperature. The cells were washed extensively with PBS and then incubated in biotinylated Goat-anti-mouse IgM antibody for 60 min at room temperature. The cells were washed again with PBS and incubated with avidin-rhodamine or avidin-fluorescein. To visualize the state of chromosomal condensation, cells were incubated with the DNA binding fluor, 4',6-diamidino-2-phenylindole (DAPI) at 5 μg/ml as described by Baron et al., *Cell Motil. and the Cytoskel.* 18: 1–14 (1991). Following extensive PBS washes, the coverslips were mounted and viewed under oil immersion with the 63× objective of a MRC-600 confocal microscope (Bio-Rad Laboratories, Richmond, Calif.) equipped with epifluorescence illumination, and photographed on Ektachrome EES film (Eastman Kodak, Rochester, N.Y.).

Immunolocalization studies using the monoclonal antibody H-5 reveal a diffuse pattern of immunoreactivity in the nucleus of MDCK cells. Control IgM shows low background fluorescence indicating the specificity of the H-5 nuclear staining. The distribution of Pol II LS is striking in daughter cell pairs that were either in the process of cytokinesis or had separated almost completely. Daughter cell pairs were identified readily by their symmetry, and by the presence of multiple, discrete, immunoreactive clusters scattered throughout the cytoplasm.

During interphase, Pol II LS is located in the nucleus. Pol II LS moves from the nucleus to discrete locations in the cytoplasm as mitosis progresses. Therefore, Pol II LS is intranuclear in non-dividing cells, migrates to the cytoplasm during mitosis, and forms extranuclear bodies in newly replicated daughter cells.

To characterize the subcellular localization of Pol II LS at each phase of the cell cycle, MDCK cells were subjected to immunofluorescence microscopy as described above. The state of chromosomal condensation, and the contours of the nuclear periphery revealed by DAPI staining indicate the phase of the cell cycle for each cell in a microscopic field. MDCK cells were photographed through one filter to reveal the chromosomal DNA and the same microscopic fields of cells were photographed through a second filter to reveal the pattern of Pol II LS immunofluorescence.

Pol II LS immunoreactivity in interphase nuclei is mostly diffuse staining with a variable degree of fine punctate staining. The punctate dots are separated from the nuclear periphery by a continuous, submembranous zone which appears to follow the contours of the nuclear envelope.

Early prophase is identified by an intense, beaded appearance of the DAPI-stained nuclei, which reflects the onset of chromosomal condensation. Coincident with this change, Pol II LS immunoreactivity intensifies and appears as intranuclear Pol II LS bodies. Close inspection of the immunofluorescent images reveal that Pol II LS forms a "shell" that coats each chromosome as it condenses. A subset of the intranuclear "bodies" are therefore actually folded, condensed chromosomes coated with Pol II LS. The outermost bodies are arranged in a line separated from the nuclear periphery by a continuous zone, which lacks discrete immunofluorescent bodies. Mid-prophase cells are identified by increasing condensation of the chromosomes and a loss of the smooth edges at the nuclear periphery indicating early nuclear envelope disassembly. Coincident with these changes, a few Pol II LS bodies begin to appear in positions outside of the disassembling nucleus. By late prophase, multiple Pol II LS bodies are dispersed widely to various positions, many of which are remote from the chromosomes.

The Pol II LS bodies remain widely dispersed throughout the cell during metaphase and anaphase. However, the chromosomes and spindle apparatus per se do not stain prominently with monoclonal antibody H-5 during these phases. However, a perichromosomal "shell" comprised of Pol II LS immunoreactivity is visible. The pattern of the Pol II LS immunoreactivity in metaphase and anaphase cells is variable: most cells are studded with discrete bodies throughout, with some Pol II LS-bodies being smaller than others, and, in other cells, Pol II LS immunofluorescence appears almost homogeneous. Metaphase and anaphase cells with either of these two staining patterns contain a distinct group of Pol II LS bodies that are positioned in a ring-like structure which surrounds the mitotic spindle apparatus. The peri-spindle Pol II LS bodies are larger and more intensely immunoreactive than the more peripheral bodies.

To determine the spatial relationship between the spindle apparatus and the ring of large, intensely immunoreactive Pol II LS bodies, double immunofluorescence was performed using monoclonal antibody H-5 and polyclonal antibodies directed at the nuclear mitotic antigen (NuMA), a 240 kDa nuclear protein that distributes to the polar regions of the spindle apparatus as described by Price and Pettijohn, *Exp. Cell Res.* 166:295–311 (1986) and Yang et al., *J. Cell Biol.* 116:1303–1317 (1992). Anti-NuMA antibodies stain the crescent-shaped poles of the spindle, and the apex of each crescent co-localizes with the centrosome. Therefore, NuMA staining marks the ends of the spindle apparatus, whereas anti-Pol II LS antibodies stain Pol II LS as it moves, during mitosis, from the nucleus to the cytoplasmic compartment where it forms discrete dot-like bodies that are bound to the peripheral cytoskeleton outside of the spindle apparatus. Anti-NuMa antibodies and anti-Pol II LS antibodies do not cross react.

Photography of the FITC-stained, NuMA-reactive spindle structures shows that the Pol II LS bodies are aligned in a ring-like arrangement, which surrounds the region of the spindle apparatus. The Pol II LS bodies do not co-localize with the spindle poles, and the area of the spindle apparatus between the spindle poles, containing microtubules and associated proteins, does not stain intensely with the anti-Pol II LS monoclonal antibody H-5.

Telophase cells appear to have a variable degree of nuclear reassembly as indicated by the contour of the nuclear periphery, which is well-defined in some telophase cells and poorly defined ("fuzzy") in others. The monoclonal antibody H-5 stained nascent nuclei in early and late stages of reassembly in addition to the cytoplasmic bodies. The Pol II LS bodies were widely distributed throughout the cytoplasm, including the tips of cell processes, which are far removed from the nucleus. The number of Pol II LS bodies is reduced in telophase cells compared to metaphase and anaphase cells. Significantly, the cytoplasmic Pol II LS bodies are present in late telophase cells and appear even in many of the daughter cells that have completed cytokinesis. Monoclonal antibody H-5 did not stain centrioles or the midbodies between separating daughter cells.

A substantial fraction of Pol II LS is tightly associated with discrete intranuclear domains As discussed above, Pol II LS has a dynamic, highly compartmentalized subcellular distribution which changes at specific times during the cell cycle and Pol II LS's targeting and cell cycle redistribution are mediated by the CTD.

There are two major fractions of Pol II LS in the nucleus: one is diffusely distributed and readily extracted; the other is non-uniformly distributed and tightly associated with 20–50 discrete "speckle domains (SDs)". Light microscopy of Pol II LS's intranuclear distribution shows discrete domains, as well as a diffusely distributed fraction of Pol II LS. Electron microscopy shows large "speckle domains (SDs)" previously shown to harbor clusters of spliceosomal proteins, called "interchromatin granule clusters (ICGCs)" when visualized at the EM level. Labeling with mAb H5 decorates multiple Pol II LS-rich domains (PRFs), some of which directly abut the ICGCs. PRFs that are not associated with ICGCs are frequently arranged in rows spanning the nucleoplasm between adjacent ICGCs.

Pol II genes are transcribed and spliced in regions that are separate from ICGCs Several studies indicate that Pol II transcription takes place in nuclear sites that are separate from ICGCs. First, EM studies indicate that the ICGCs are weakly labeled following [$^3$H] uridine pulses. Second, labeling with 5' bromouridine 5' triphosphate showed that nascent Pol II transcripts are produced in 100–500 discrete foci distributed throughout the nucleus. These transcription foci are separate from the regions most enriched with SC35, the ICGCs. Third, in situ hybridization studies showed that transcripts of some genes are located immediately adjacent to ICGCs, but most are clearly separate from ICGCs. Taken together, these data indicate that Pol II transcription takes place in discrete intranuclear sites that are separate from ICGCs.

Functional Role of RNA Pol II

Pre-mRNAs are spliced as they are synthesized by RNA polymerase II

The protein encoding genes in eukaryotic cells are transcribed by RNA polymerase II. Nascent Pol II transcripts (i.e., pre-mRNAs) are modified by a series of reactions such as 5' capping, splicing and polyadenylation to produce mRNAs, which are exported to the cytoplasm and translated into proteins. In multiple eukaryotic systems, introns appear to be spliced at the same time that more downstream segments of the pre-mRNA are being synthesized by Pol II, that is, pre-mRNAs are spliced co-transcriptionally. Pre-mRNA splicing is spatially and temporally linked to Pol II transcription, although it is still unclear how spliceosomes are recruited to nascent transcripts.

Splicing macromolecules are stored in ICGCs

Proteins and snRNAs that participate in splicing are concentrated in 20–50 irregularly-shaped regions termed "speckle domains (SDs)." SDs can be visualized by immunofluorescence (IF) microscopy using antibodies directed against snRNPs, and non-snRNP slicing proteins of the SerArg (SR) family. SR proteins, such as SC35 (35 kDa) and B1C8 (180 kDa), have domains formed of interrupted clusters of Ser/Arg repeats (usually approximately 50 residues) which are variably phosphorylated on serine. SDs can also be visualized by fluorescent in situ hybridization (FISH) using oligonucleotide probes complementary to spliceosomal snRNAs, and by IF using antibodies directed at the trimethyl-guanosine cap (αTMG) on the 5' end of snRNAs U1, U2, U4 and U5. At the ultrastructural level, speckle domains are termed "interchromatin granule clusters" or "ICGCs".

Splicing macromolecules undergo a transcription-dependent redistribution cycle When transcription is inhibited, snRNP proteins, snRNAs and SR splicing proteins accumulate in the ICGCs, which enlarge and coalesce. Simultaneously, there is reduced SR immunolabeling in nuclear regions surrounding the ICGCs. It is widely believed that splicing complexes redistribute from these regions to the ICGCs, where they are stored. Splicing complexes can be recruited from the ICGCs to the surrounding nucleoplasm, where most splicing is believed to take place.

Pol II LS also undergoes a transcription-dependent redistribution cycle

In transcriptionally active nuclei, a subpopulation of Pol II appears to co-localize with clusters of splicing proteins in 20–50 'large' domains, which are readily visualized under the light microscope. On close inspection, one also observes hundreds of smaller Pol II-rich domains that do not co-localize with the clusters of splicing proteins. Evidence indicates that the 'large' Pol II-rich domains are storage/reassembly sites, and that the 'small' Pol II-rich domains are pre-mRNA synthetic sites.

In transcriptionally active nuclei, Pol II LS is associated with 20–50 'large' domains as well as hundreds of 'small' domains. During states of transcriptional inhibition, Pol II LS redistributes from the 'small' domains to the 20–50 'large' domains, which become enlarged and round. When the cells are released from transcriptional inhibition, Pol II LS and splicing proteins redistribute back to the 'active' speckled pattern. Pol II LS's intranuclear redistribution cycle is reversible and temperature dependent.

The greater than $10^2$ 'small' domains appear to be sites where Pol II LS produces pre-mRNAs. Nascent pre-mRNA transcripts were labeled for 15 minutes with 5'BrUTP in a nuclear 'run on' experiment. Under these conditions, only nascent RNA (not DNA) is labeled. Using anti-5' BrU antibodies, the nascent transcripts appear to co-localize precisely with the small Pol II LS domains, but not with the large domains. Other groups have recently shown that nascent pre-mRNAs arise in approximately $10^2$ discrete domains that look identical to the 'small' Pol II LS rich domains. These data agree with many other studies showing that the pre-mRNAs synthesis occurs outside of the ICGCs.

Characterization of Pol II LS

Nuclear proteins are traditionally classified by function, subcellular localization, or biochemical properties. For example, nuclear matrix proteins are often tightly associated with a specific fraction of the chromatin as reflected by a high degree of insolubility, defined operationally by sequential biochemical extractions. Most nuclear matrix proteins remain entirely in an insoluble fraction when cells are treated with buffers containing detergents such as TRITON X-100 surfactant or deoxycholate.

In contrast, a significant fraction of Pol II LS in MDCK cells is solubilized by relatively mild extraction conditions. (0.5% TRITON X-100 surfactant, 0.5% sodium deoxycholate [DOC]). Mild extraction conditions are defined herein as extractions procedures that do not require the use of sodium dodecyl sulfate and include the extraction procedure described in detail below.

Pol II LS was extracted from MDCK cells grown to confluency in cell culture dishes (150 mm in diameter). Cell monolayers were washed twice with cold TBS and rocked for 15 minutes at 4° C. in 5 ml of TRITON X-100 surfactant/DOC dilution buffer containing 10 mM $Na_2HPO_4$/$NaH_2PO_4$, pH 7.2, 150 mM NaCl, 0.5% TRITON X-100 surfactant, 0.5% sodium deoxycholate, 1 mM phenylmethyl-sulfonyl fluoride (PMSF), 2 mM $NaN_3$, 0.2 mM $Na_3VO_4$, 5 mM EDTA (ethylene diamine tetraacetic acid) and 2 mM EGTA. The majority of Pol II LS partitions in the TRITON X-100 surfactant/DOC-soluble fraction. The relatively mild conditions required to expose the H-5 epitope of Pol II LS in immunofluorescence experiments is paralleled by its solubility properties. Pol II LS is readily extracted from cells with nonionic detergents, indicating that Pol II LS is not a nuclear matrix protein, at least by operational biochemical criteria.

Immunoaffinity Purification of Pol II LS

Pol II LS can be purified by affinity chromatography using one or a combination of antibodies covalently bound to agarose beads or bound non-covalently via a Goat-anti mouse IgM antibody to Staphylococcus aureus protein G beads (Sigma, Chemical Co., St. Louis, Mo.). Most preferably, Pol II LS is purified by affinity chromatography using the H-5 monoclonal antibody.

Pol II LS isolation is achieved by incubating cell extracts, such as the MDCK cell extracts described above, with an anti-Pol II LS monoclonal antibody, such as the monoclonal antibody H-5, attached to a solid phase, such as chemical conjugation to agarose beads. After incubation, the beads are washed, denatured and resolved on a polyacrylamide gel. Pol II LS purified from less than 50 mg of total MDCK cell protein is visible as a 240 kDa band stained with coommassie brilliant blue.

Pol II LS can be isolated from the cells and tissues of a wide variety of eukaryotic species as set forth below, thus facilitating biochemical and immunoaffinity purification.

Pol II LS Genes

Clones encoding Pol II LS have been identified fm from a number of sources including human (Winzerith et al., *Nucleic Acids Research* 20, 910 (1992), Accession No. X63564; Mita, Accession No. X74870). Genes encoding Pol II LS have been identified from a number of other sources, including *Trypanosoma brucei* (Evers et al., Cell 56, 585–597 (1989), Accession No. X13491), *Mus musculus* (Ahearn et al., *J. Biol. Chem.* 262, 10695–10705 (1987), Accession No. A28490; Corden et al., *Proc. Natl. Acad. Sci. USA* 82, 7934–7938 (1985), Accession No. A23566), chicken (Allison et al., *Mol. Cell. Biol.* 8, 321–329 (1988), Accession No. P11414), *C. elegans* (Bird and Riddle, *Mol. Cell. Biol.* 9, 4119–4130 (1989), Accession No. A16356), *Drosophila melanogaster* (Jokerst et al., *Mol. Gen. Genet.* 215, 266–275 (1989); Biggs et al., *Cell* 42, 611–621 (1985); and Allison et al. (1988); Accession No. P04052), Arabidopsis (Dietrich et al., *Plant Mol. Biol.* 15, 207–223 (1990), Accession No. X52494), and yeast.

It will be understood that one skilled in the art can obtain the nucleotide and amino acid sequences encoding Pol II LS from other organisms, including yeast, using standard cloning procedures. Known Pol II LS nucleotide sequences, both disclosed herein and known in the art, can be used, for example, as a nucleotide probe or primer for the isolation of genes for yeast Pol II LS, human Pol II LS or any other organism expressing Pol II LS by methods well known to those skilled in the art. It will be understood by those skilled in the art that, in order to increase the chances of hybridization of a probe or primer to a human nucleic acid sequence, the third base of one or more codons could be changed, in such a way that the amino acid encoded by that codon is not changed. For example, the third base of each codon in a probe could be substituted with inosine.

Fragments containing sequences unique to Pol II LS can be used as nucleotide probes or primers for Pol II LS. A nucleotide probe or primer is defined herein as a nucleotide molecule that includes a sufficient number of nucleotides to specifically hybridize under standard hybridization conditions to DNA or RNA that includes identical or closely related sequences of nucleotides. Preferably, probe hybridization is conducted under stringent conditions. A probe or primer may include any number of nucleotides and may include as few as approximately 10 and as many as hundreds of thousands of nucleotides. It is well known in the art that probes or primers preferably have a length of approximately 16 to 18 consecutive nucleotides or greater. One skilled in the art looking for a suitable Pol II LS probe or primer would simply conduct a computerized search of genetic databases to unique fragments within the 16 to 18 nucleotide length range having homologous nucleotide sequences to the Pol II LS nucleotide sequence. One would then choose a region different from or a length longer than that of the longest homologous sequence to define a unique fragment, determine optimal hybridization conditions for the selected fragment, attach a detectable label to the fragment, and use the labelled fragment as a hybridization probe for Pol II LS. The conditions and protocols for such hybridization reactions are well-known to those of skill in the art, as are the effects of probe size, temperature, degree of mismatch, salt concentration and other parameters on the hybridization reaction. For example, the lower the temperature and higher the salt concentration at which the hybridization reaction is carried out, the greater the degree of mismatch that may be present in the hybrid molecules.

As used herein, all assays, and procedures, such as hybridization reactions and antibody-antigen reactions, unless otherwise specified, are conducted under conditions recognized by those skilled in the art as standard conditions. Hybridization conditions are described by Sambrook, Frisch & Maniatis, *Molecular Cloning: A Laboratory Manual*, 2nd Ed., (Cold Spring Harbor Laboratory, N.Y. 1989), the teachings of which are incorporated herein by reference.

The largest subunit of RNA Polymerase II (Pol II LS) has an unusual but highly conserved COOH-terminal domain (CTD)

All eukaryotic Pol II LS molecules have a structure called the "COOH-terminal domain" or "CTD", which is comprised of tandemly repeated heptapeptides similar or identical to the consensus sequence, $Tyr^1Ser^2Pro^3Thr^4Ser^5Pro^6Ser^7$ (SEQ ID NO. 1)(FIG. 1A). Mammalian Pol II LS has 52, Drosophila Pol II LS has 44 and *S. cerevisiae* Pol II LS (RPB1) has 26 repeats. The Tyr and Pro residues at positions 1, 3 and 6 are retained in all heptapeptide repeats (see FIG. 1A). The upstream half of the CTD in all eukaryotic Pol II LS molecules is formed of mostly consensus repeats, whereas the downstream half of the CTD is predominantly variant repeats, as shown in FIG. 2A. The last 10 residues are not highly conserved, and they are dispensable for Pol II transcription.

CTD peptides target molecules to SDs

A series of plasmids encoding Flag-tagged CTD peptides containing 1, 3, 6, 13, 26, 32 and 52 heptapeptides were prepared, as shown in FIG. 2B. The Flag epitope is [AspTyrLys(Asp)$_4$Lys] (SEQ ID NO. 20). An indicator protein, β-galactosidase, was also used. These were transfected into COS, CV1 and HeLa cells, which were subsequently solubilized and immunoblotted with anti-CTD mAbs H5 and H14, and the anti-Flag peptide mAb M2. mAb M2 was used to chart the distribution of the Flag-CTDs; and mAb B1C8 was used to chart the distribution of the SerArg splicing protein B1C8, an inhabitant of the ICGCs.

Truncated CTD peptides retain a targeting activity that is distinct from the full length CTDs.

The truncated CTD fusion proteins were examined for their ability to enter the nucleus and to localize to discrete domains. The preliminary results are tabulated at the left of each construct in FIG. 2B. All CTDs tested can enter the nucleus without a NLS. The ability to target an indicator protein to discrete domains is scored 'Yes,' 'No' or 'NYT'. Many of the CTD peptides are targeted to nuclear domains abutting or overlapping regions enriched with splicing proteins (i.e. ICGCs), but they also appear in the nucleoplasm surrounding the ICGCs.

CTD peptides induce a dramatic reorganization of ICGs in vivo.

For each construct, the B1C8 pattern was assessed in approximately 150 transfected nuclei. Transfected nuclei were scored as "unchanged ICGCs" or "reorganized ICGCs." Reorganized ICGCs fall into two categories: (i) total dispersal of B1C8; and (ii) shrinkage of ICGCs plus dispersal of B1C8 staining.

Figure 3:
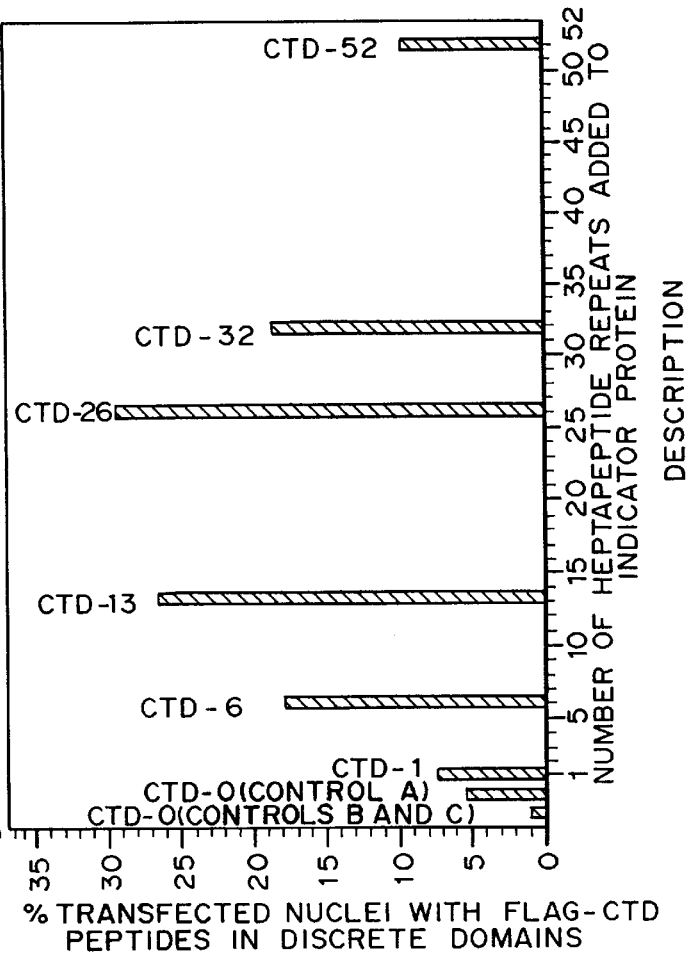
FIG. 3 is a schematic of the speckle-localizing properties of flag-tagged CTD peptides, plotting % transfected nuclei with Flag-CTD peptides in discrete domains versus number of heptapeptide repeats added to indicator protein. The "heptapeptide-like" sequence shown is also set forth in SEQ ID NO. 24. The sequences which are shown as repeat 1 through repeat 6 are also set forth in SEQ ID NO. 4; SEQ ID NO. 6; SEQ ID NO. 5; SEQ ID NO. 1; SEQ ID NO. 1; and, SEQ ID NO. 2, respectively.

As shown by FIGS. 2B and 3, all CTD peptides (including $CTD_1$) bestow speckle localizing activity on indicator peptides. A heptapeptide-like sequence located immediately upstream of the 'true' heptapeptide #1 must be removed to eliminate all speckle localizing activity from control peptide A.

Thus, control peptides B and C lack speckle-localizing activity. Another control peptide, including seven tandem repeats of the heptamer $Y_1P_2S_3T_4S_5P_6S_7$ (SEQ ID NO. 25)(Pro and Ser switched at positions 2 and 3) has low speckle-localizing activity compared to Flag-$CTD_6$. These studies firmly establish that multiple control peptides lack significant speckle-localizing properties, and that all CTD-containing peptides possess this property.

Serially Truncated Flag-Tagged CTDs differ in their speckle-localizing properties The targeting properties of serially truncated CTD peptides are different, as shown in FIG. 3. First, note that targeting activity increases as consensus heptapeptides are added to Flag-$CTD_1$, and it reaches a maximum at Flag-$CTD_{26}$, which is comprised of the upstream one-half of the CTD (that is, nearly all consensus repeats).

The speckle-localizing activity declines as natural downstream variant repeats are added to the COOH terminus of Flag-$CTD_{26}$, as shown in FIG. 3. The decline seems to be proportional to the number of variant heptads added (a "dose-dependent" phenomenon). As variant repeats are added the Flag-CTDs may become more competent to redistribute from the storage domains to the diffuse nucleoplasm where the genes are transcribed and spliced. Consistent with this idea, F-$CTD_{52}$ has lower speckle-localizing ability than shorter CTD peptide, but it is fully competent to redistribute to enlarged speckle domains when the cells are treated with transcriptional inhibitors, similar to endogenous Pol II LS. A substantial fraction of endogenous Pol II LS resides in the diffuse nucleoplasm, and redistributes to the speckles in all transcriptionally inhibited cells.

$CTD_{26}$, $CTD_{13}$, and $CTD_6$ target the Flag peptide to discrete domains better than longer CTDs. The subnuclear distribution of F-$CTD_6$ was compared to that of B1c8, a 180 kDa SerArg splicing protein. The digital images were taken with a CCD camera. B1C8 labeling is pseudocolored green, whereas mAb M2 labeling is pseudocolored red. When the two images are superimposed, it is clear that F-$CTD_6$ does not co-localize with B1C8. Rather, the F-$CTD_6$ peptide is most concentrated in discrete domains that directly abut the B1C8-labeled speckles (i.e. ICGCs). The close proximity of F-$CTD_6$ and B1C8 containing domains is strikingly similar to the type 1 PRFs (mAb H5 labeling) and the ICGCs visualized by IEM. These data suggest strongly that the F-$CTD_6$ peptide is targeted to PRFs that are inhabited by a subset of endogenous Pol llo molecules.

Short CTDs, derived from the consensus-rich (upstream) half of the CTD, preferentially target indicator peptides to 'storage depots,' where they are essentially stranded, whereas the full length CTDs retain the ability to redistribute between the 'storage' sites and the sites where Pol II transcribes genes ("round trip ticket").

CTD peptides induce a dramatic reorganization of ICGs in vivo

Figure 4:
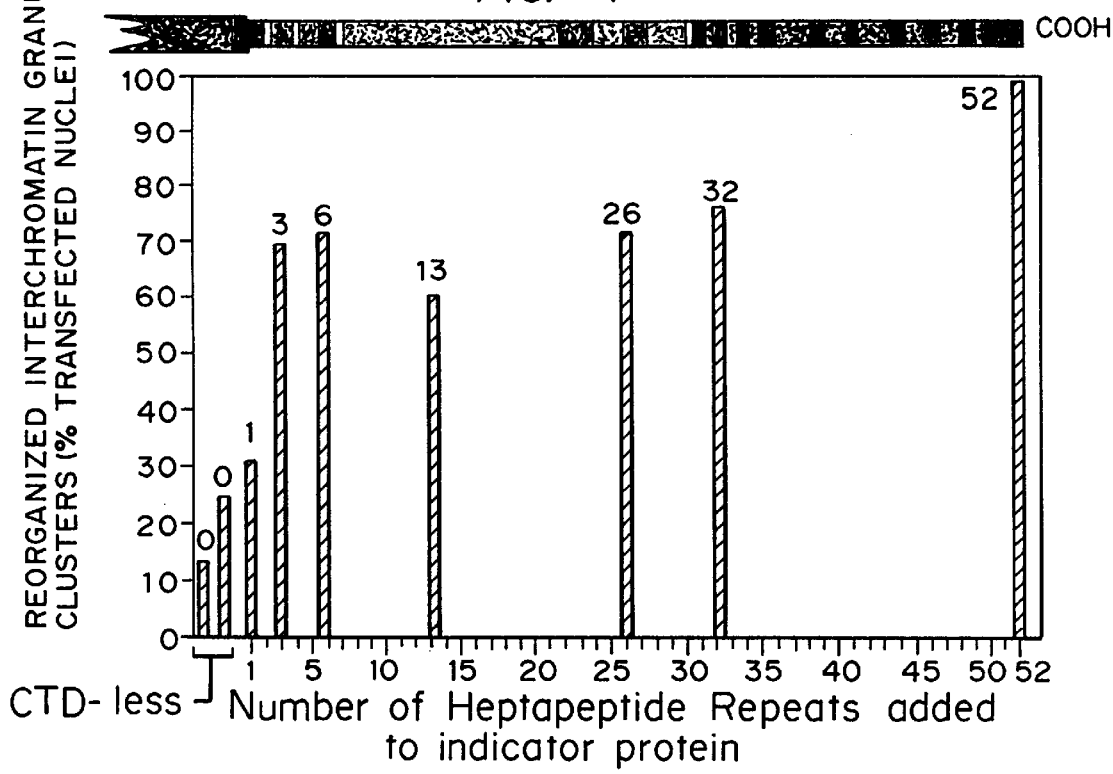
FIG. 4 is a schematic of recombinant CTD peptides inducing reorganization of splicing molecules in vivo, plotting reorganized interchromatin granule clusters (% transfected nuclei) versus number of heptapeptide repeats added to indicator protein.
Figure 5:
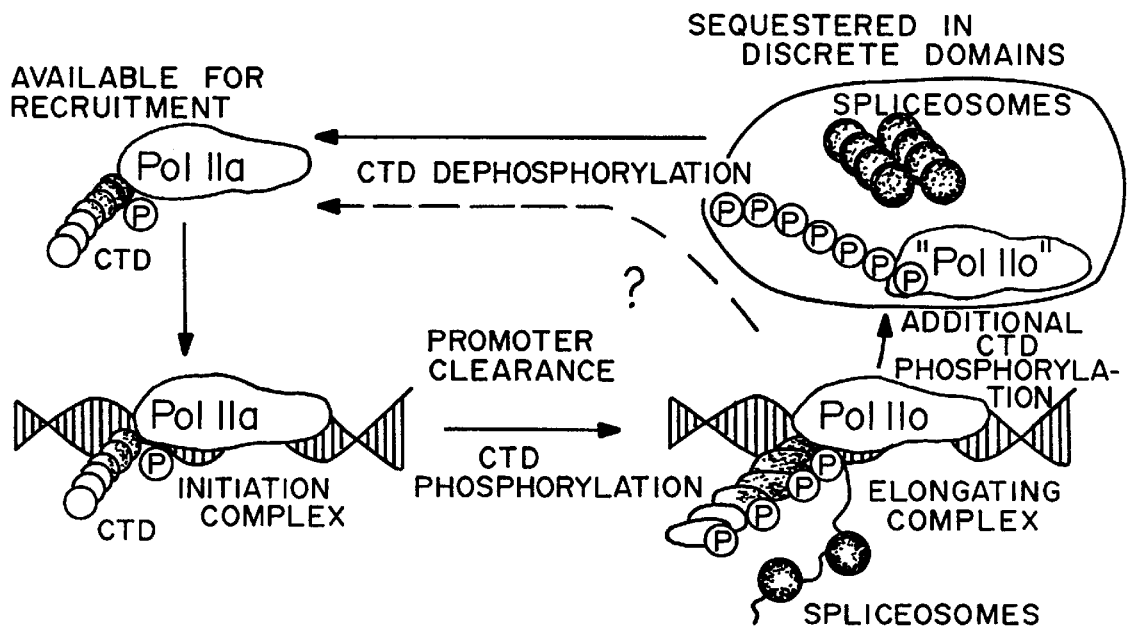
FIG. 5 is a schematic of transcription and redistribution cycles of RNA polymerase II mediated by reversible phosphorylation of the CTD.

FIG. 4 shows that F-$CTD_3$, F-$CTD_6$, F-$CTD_{13}$, F-$CTD_{26}$, F-$CTD_{32}$, and F-$CTD_{52}$ induce a reorganization of the B1C8 stained ICGCs. Furthermore, the ICGC-disrupting ability increases in proportion to the number of heptapeptides. F-CTD52 is the most potent ICGC-disrupting agent (approximately 100%). Short CTDs (e.g. F-$CTD_3$ and F-$CTD_6$) typically have less dramatic effects on the organization of ICGCs. Similar results were obtained with antibodies directed at other splicing proteins in the ICGCs.

Note that there is a sharp increase in CGCC-disrupting activity between F-$CTD_1$ and F-$CTD_3$, as shown in FIG. 4. This result shows that even the first three heptapeptide repeats (21 amino acids) can induce partial reorganization of the ICGCs in vivo. None of the control peptides induce this effect, even when expressed at high levels in the nucleus.

Effect of Phosphorylation of CTDs

Pol II LS's CTD is either hyperphosphorylated or hypophosphorylated in vivo

All known phosphorylation sites are in Pol II LS's CTD. In mammalian cells, there are two major forms of Pol II LS (FIG. 1B): "Pol IIo" is hyperphosphorylated predominantly on Ser/Thr residues at positions 2, 4, 5 and 7 of the CTD heptapeptide repeats, and migrates at approximately 240 kDa. "Pol IIa" is relatively hypophosphorylated and migrates at approximately 220 kDa. Because 241 of the 365 amino acid residues in the CTD are phosphorylatable (128 serines, 61 threonines and 52 tyrosines), there is potential for a vast array of differentially phosphorylated species of Pol II LS. Nevertheless, very few Pol II LS molecules migrate between 220 and 240 kDa in vivo; the majority of Pol II LS is either Pol IIo or Pol IIa. The implication is that intermediately phosphorylated Pol II LS species are rapidly converted to Pol IIo or Pol IIa.

Figure 1B:
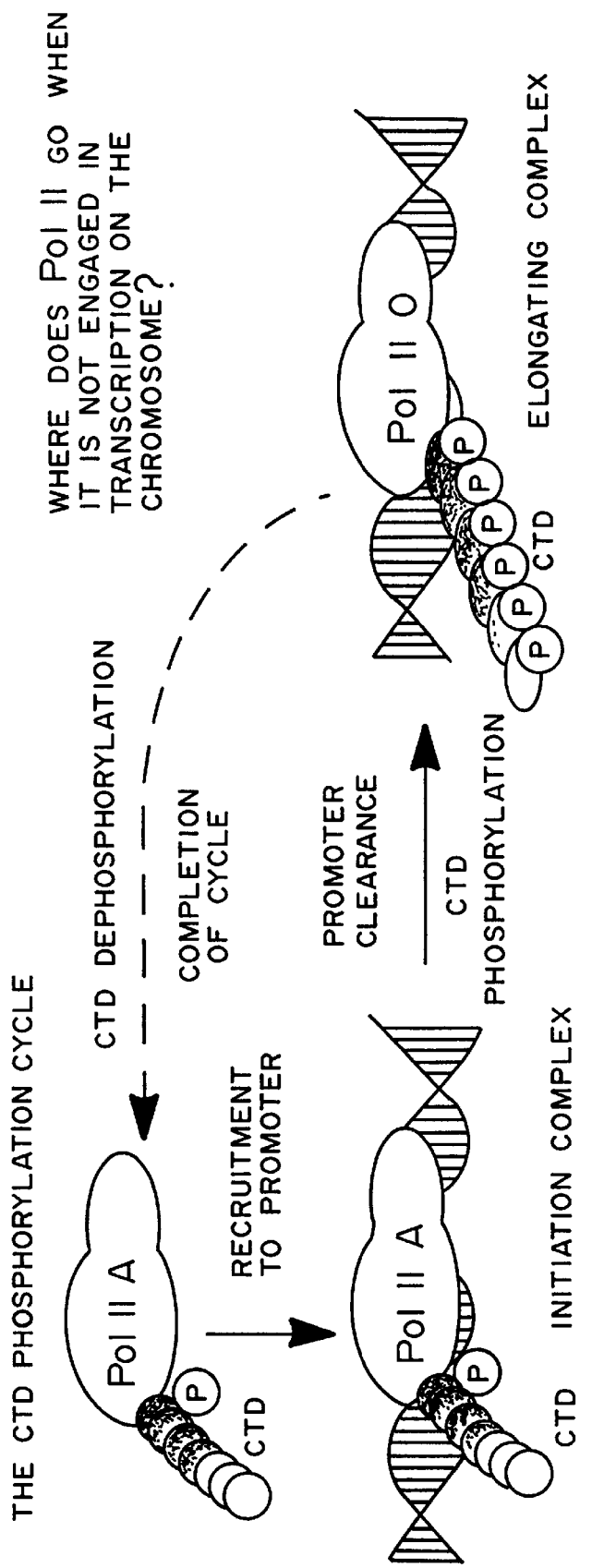
FIG. 1B is a schematic of the CTD phosphorylation cycle.

Pol II LS's CTD is hyperphosphorylated at the onset of transcriptional elongation CTD phosphorylation has been studied almost exclusively in in vitro transcription assays. Pol IIa is efficiently recruited to transcription initiation complex in vitro, and the elongation phase is heralded by phosphorylation of the CTD to yield Pol IIo. In vivo, paused polymerases are primarily Pol IIa, but they are converted to Pol IIo as they enter the elongation phase. These studies imply that Pol II LS's CTD undergoes a phosphorylation/dephosphorylation cycle which regulates (or reflects) Pol II's cycle of transcriptional initiation, elongation, termination and re-initiation. This well-accepted model is shown in FIG. 1B.

The fate of Pol IIo molecules after the elongation phase is unknown, although the studies described herein demonstrate that Pol IIo can be stored. Therefore, hyperphosphorylation of the CTD does not necessarily indicate that Pol II LS is engaged in transcriptional elongation. The level of Pol IIo remains unchanged throughout the cell cycle, including mitosis, when transcription is shut off. A subset of Pol IIo molecules is tightly sequestered in non-chromosomal locations inside and outside of the nucleus. The studies described herein indicate that the CTD plays a pivotal role in Pol II LS's dynamic, cell cycle regulated redistribution between storage sites and the sites of pre-mRNA synthesis.

A cyclin dependent kinase phosphorylates Pol II LS's CTD on Ser/Thr residues.

Several kinases phosphorylate CTD heptapeptides in vitro. Roy et al, *Cell* 79, 1093–1101 (1994), reported that the cyclin H-dependent kinase, cdk7 (also called cdc2/cdk2 activating kinase or 'CAK' and 'M015') is the CTD kinase in the transcription factor IIH (TFIIH), an integral part of the Pol II transcriptional initiation complex. Feaver et al, *Cell* 79, 1103–1109 (1994), showed that KIN28, a yeast cyclin dependent kinase, phosphorylates Pol II LS's CTD in *S. cerevisiae*, and that it is part of the TFIIH complex in yeast. Cdk7/KIN28 is likely to be a physiological CTD kinase, because it associates directly with Pol II transcription initiation complexes, and Pol II-mediated transcription in vitro and in vivo requires cdk7/KIN28. The exact functional consequence(s) of cdk7/KIN28-catalyzed phosphorylation of the CTD remain unknown, but it has recently been shown by Akoulitchev, et al., *Nature* 377, 557–660, that cdk7 is necessary for transcriptional elongation in vitro.

Genetic studies indicate functional redundancy within Pol II LS's CTD, but do not determine the role played by CTD heptapeptides.

Genetic studies indicate that the CTD is essential for Pol II transcription in vivo, but nearly half of the CTD can be removed from the COOH end before Pol II loses its ability to maintain viability of yeast and mammalian cells. Serial deletion of heptapeptide repeats from the COOH terminus leads to graded defects in Pol II's ability to respond to transcriptional activators in vivo. Using complementation, Koleske, et al., *Trends in Biochemical Sciences* 20, 113–116 (1995), has identified multiple yeast genes that suppress the truncated CTDs (Suppressors of RNA Polymerase B [SRBs]). Mammalian SRB counterparts have yet to be identified.

Mammalian CTD mutants deleted from the COOH end also exhibit graded defects. Bartolomei et al, *Mol. Cell. Biol.*, 8, 330–339 (1988), used a cell survival assay to determine which Pol II CTD truncation mutants retain transcriptional competency: CTDs with 52 to 36 heptapeptide repeats conferred survival equally; CTDs with 36 to 26 repeats were viable, but cell growth was retarded. CTDs with 25 or fewer repeats were nonviable. CTDs with 52, 65 and 78 repeats were biologically indistinguishable in the cell survival assay, indicating that marked extension of the CTD is functionally well-tolerated. The above studies point to an essential role for the CTD. Furthermore, the heptapeptides are extensively phosphorylated and they appear to be functionally redundant. However, these approaches did not reveal how or why partial truncation of the CTD leads to partial activity.

When expressed in vivo, isolated CTD) proteins are phosphorylated, yielding two major forms analogous to Pol IIo and Pol IIa.

Given the findings that hyperphosphorylation of the CTD correlates with Pol II LS's localization to discrete domains, it was determined if isolated CTD peptides are hyperphosphorylated in vivo.

MAbs H5 and H14 recognize specific phosphorylated epitopes on Pol II's CTD, as described in U.S. Ser. No. 08/348,718. Using these mAbs it was shown that Flag-Tagged CTDs with 6, 13, 26, 32 and 52 repeats are phosphorylated in vivo. In some cases, two major forms of a given F-CTD are present: a hyperphosphorylated form ("F-CTD-O") and a hypophosphorylated form ("F-CTD-A"). Doublet bands are best recognized by mAb H14, indicating that both contain phosphorylated consensus heptapeptide repeats (YSPTSPS). MAb H5 tends to bind better to the hyperphosphorylated form (i.e., the 'O' form) of each CTD, similar to its selective reactivity to Pol IIo in vivo.

Thus, most of the recombinant F-CTDs are modified by CTD kinase(s) in vivo. The longer recombinants (F-CTD-26, F-CTD-32 and F-CTD-52) exist as a doublet comprised of hyper- and hypophosphorylated forms. The latter observation, and the paucity of intermediately phosphorylated forms, suggest that F-CTDs are processively phosphorylated in vivo, similar to endogenous Pol II LS.

Pol II LS's CTD interacts directly with multiple proteins harboring the SerArg dipeptide motif CV1 cells were transfected with Flag-Tagged CTD fusion proteins described in FIG. 4. After 24 hours, the cells were fixed and immunostained with: (i) mAb B1C8 which recognizes an approximately 180 kDa SerArg splicing protein in the ICGCs (Green); and (ii) mAb M2 which recognizes the Flag epitope on the FlagTagged CTD constructs (Red). The Flag-Tagged CTD peptides distribute mainly to discrete domains; however, a fraction of these peptides is distributed diffusely in the nucleoplasm. There is very good evidence that mAb M2 binding to the Flag epitope is favored by phosphorylation of the CTD sequence attached to the epitope. Therefore, the mAb M2 selectively recognizes the hyperphosphorylated population of FlagTagged CTD peptides, which is concentrated in the discrete sites.

The tendency of long (variant heptad-rich) F-CTDs to be diffusely distributed seems to indicate that they are stored less effectively than short (consensus heptad-rich) F-CTDs. Data showing that elevated expression of CTD peptides induces a variable disruption of the splicing domains (ICGCs) in vivo show that long (variant heptad-rich) CTDs have more potent ICGC-disrupting ability than short CTD peptides. These experiments indicates that certain CTD peptides can directly interact with molecules in the spliceosomes in vivo thereby leading to their reorganization.

Recent data suggest that F-CTD peptides may indeed bind directly to proteins in the SerArg family of splicing proteins. This may help explain why CTD peptides disrupt the ICGCs. One should therefore be able to prepare macromolecular complexes containing SerArg splicing proteins and Flag-CTD peptides. Regardless of the mechanism by which F-CTDs induce disruption of the CTDs, the immunofluorescence results show that Flag-Tagged CTD peptides are targeted to the discrete subnuclear compartment where pre-mRNAs are synthesized and spliced. Similar results have been obtained with βGal-CTD fusion proteins.

The results show that Pol II LS's CTD interacts directly with multiple proteins harboring the SerArg dipeptide motif. The localization studies of endogenous Pol II LS using epitope-tagged CTD peptides show that CTD peptides have a striking ability to "target" indicator proteins to discrete nuclear domains enriched with ICGCs, sites harboring abundant SerArg family proteins.

The data indicates that the CTD is a critical link between Pol II transcription complexes and the splicing machinery. RNA polymerase II and the splicing proteins may be stored in common or overlapping compartments, and may be coordinately recruited from these domains to the sites of pre-mRNA synthesis.

Flag-Tagged $CTD_{52}$ is targeted to domains inhabited by endogenous Pol II LS

COS cells were transfected with $pF-CTD_{52}$, fixed and double immunostained with anti-Flag mAb M2 (IgG) and mAb H5, an IgM that recognizes CTD heptapeptides in the endogenous Pol II LS and in the $F-CTD_{52}$ peptide. The speckled pattern of mAb H5 is identical to the speckled pattern of mAb M2. Certain Flag-Tagged control proteins (e.g., the N-terminal segment of Pol II LS, the Pol II segment upstream of the CTD and FlagTagged β-gal) enter the nucleus, but they are not localized to speckles. Based upon these experiments and other data, it appears that the CTD is sufficient to enter the nucleus without a conventional nuclear localization signal. The CTD concentrates the Flag peptide in sites coinciding with endogenous Pol II LS.

The $CTD_{52}$ peptide mediates transcription-dependent and redistribution that coincides spatially and temporally with endogenous Pol II LS It was then determined whether the $F-CTD_{52}$ peptide undergoes transcription dependent redistribution similar to Pol II LS. To test this idea, $pF-CTD_{52}$ transfected cells were treated for 3 hrs with the transcriptional inhibitor, DRB. As shown by immunofluorescence studies, $F-CTd_{52}$ redistributes from a finely stippled distribution to a smaller number of enlarged speckle domains, which coincide with Pol IIo-enriched domains. Similar results were obtained with α-amanitin, which neither binds to nor induces dephosphorylation of the CTD. Similar results have also been obtained with $β-Gal-CTD_{52}$.

Rational Design of CTD Targeting Modules with Different Pharmacological Properties A key factor is the recognition that not all heptapeptides in eukaryotic CTDs are equivalent structurally and functionally. The properties of a repetitive polymer formed of multiple tandemly arranged heptapeptides will be determined by the number of heptapeptides; the ratio of consensus to variant heptapeptides; their relative arrangement in the polymer; and the phosphorylation state of each heptapeptide. Using this information, one can control the bioavailability of the pharmacological agent being targeted to Pol II genes or to the associated splicing apparatus. For example, some synthetic "mini-CTDs" may be used to target the therapeutic agent preferentially to a 'storage' domains, with a limited ability to redistribute to the Pol II genes and active splicing machinery. Other CTD targeting modules may be constructed with features that allow them to more readily exit the 'storage' compartments (PRFs). The latter CTD modules would be more bioavailable to the Pol II transcription and splicing machinery.

The targeting modules may be constructed from one or more heptapeptide units, which are derived from natural sources (any species of Pol II LS molecule). To achieve a particular pharmacological property, one would make derivative CTD modules. Such derivatives would differ from the natural CTD sequence in terms of relative abundance of a particular heptapeptide, the ratio of consensus to variant heptapeptide and the order in which various heptapeptide units appear in the derivative. Such derivative CTD modules may be partly derived from natural CTD heptapeptide sequences, and partly derived from non-Pol II LS sequences. Using the unit heptapeptides as building blocks, one should be able to create a large spectrum of intranuclear partitioning modules, that differ subtly in their pharmacological properties.

Definition of a CTD heptapeptide

As defined herein, a CTD heptapeptide is any sequence of seven amino acid residues that shares the following consensus: sequence :$Y_1X_2P_3X_4X_5P_6X_7$ (SEQ ID NO. 21). (X is usually=S or T, which are phosphorylatable residues, but it may be any other amino acid residue). heptapeptides can be used as building blocks for the CTD peptides:

| YSPTSPS | YSPTSPN | YTPTSPN | YSPTSPA | YTPOSPS |
|---------|---------|---------|---------|---------|
| YEPRSPGG | YSPTSPT | YSPTSPK | YTPTSPK | YSPTTPK |
| YSPTSPV | YSPTSPG | YSLTSPA | YTPSSPS | YSPSSPS |
| YTPTSPS | YSPSSPE | YTPOSPT | YSPSSPR | |

Note: underlined residues vary from the consensus YSPTSPS.
**Key for single letter amino acid designations. The following single letter amino acid abbreviations are used herein.

| A = alanine | D = aspartic acid | Q = glutamine |
|---|---|---|
| I = isoleucine | R = arginine | C = cysteine |
| G = glycine | L = leucine | N = asparagine |
| E = glutamic acid | H = histidine | K = lysine |
| F = phenylalanine | F = phenylalanine | T-theronine |
| Y-tyrosine | F = phenylalanine | S = serine |
| W = tryptophan | V = valine | |

Thus, in the mammalian Pol II LS CTD, the heptapeptides set forth in SEQ ID NO. 1 through SEQ ID NO. 19 can be used as building blocks for the CTD peptides.

All heptapeptides that follow the $Y_1X_2P_3X_4X_5P_6X_7$ (SEQ ID NO. 21) consensus pattern can be used, regardless of the species of origin. This includes all heptapeptides that are absent in human Pol II LS, but present in the Pol II CTD of other eukaryotic species: Drosophila; Arabidopsis (plant); C. elegans (nematode); yeast (S. cerevisiae and S. pombe); and plasmodium spp.

All heptapeptides that follow the $Y_1X_2P_3X_4X_5P_6X_7$ (SEQ ID NO. 21) consensus pattern are expected to have some partial targeting action, or modify the targeting action of other heptapeptides. Any tandemly arranged combination of the aforementioned heptapeptides can also be used as a "targeting module".

Labelling of Peptides

Pol II LS peptides, most preferably CTD peptides, can be directly or indirectly labelled with a detectable label to facilitate detection of the presence of the peptides by detection of the label. Various types of labels and methods of labelling antibodies are well known to those skilled in the art. Several specific labels are set forth below.

For example, the peptide can be labelled directly or indirectly with a radiolabel such as, but not restricted to, $^{32}P$, $^{3}H$, $^{14}C$, $^{35}S$, $^{125}I$, or $^{131}I$. The radiolabel is generally attached by chemical modification. Detection of a label can be by methods such as scintillation counting, gamma ray spectrometry or autoradiography.

Fluorogens can also be used directly or indirectly to label the CTD peptides. Examples of fluorogens include fluorescein and derivatives, phycoerythrin, allo-phycocyanin, phycocyanin, rhodamine, Texas Red or other proprietary fluorogens. The fluorogens are generally attached by chemical modification and can be detected by a fluorescence detector.

The CTD peptide can alternatively be labelled directly or indirectly with a chromogen to provide an enzyme or antibody label. For example, the peptide can be biotinylated so that it can be utilized in a biotin-avidin reaction which may also be coupled to a label such as an enzyme or fluorogen. For example the peptide can be labelled with peroxidase, alkaline phosphatase or other enzymes giving a chromogenic or fluorogenic reaction upon addition of substrate.

Additives such as 5-amino-2,3-dihydro-1,4-phthalazinedione (also known as Luminol™) (Sigma Chemical Company, St. Louis, Mo.) and rate enhancers such as p-hydroxybiphenyl (also known as p-phenylphenol) (Sigma Chemical Company, St. Louis, Mo.) can be used to amplify enzymes such as horseradish peroxidase through a luminescent reaction; and luminogeneic or fluorogenic dioxetane derivatives of enzyme substrates can also be used. Such labels can be detected using enzyme-linked immunoassays (ELISA) or by detecting a color change with the aid of a spectrophotometer.

Coupling of Bioactive Agents

Any of a variety of bioactive agents may be attached to the RNA Pol II LS or CTD peptides, referred to collectively as "Peptide", to permit delivery of the bioactive molecule to the nucleus. In the preferred embodiment, described below, the bioactive agent is an oligonucleotide, most preferably antisense or a ribozyme. For example, the Peptides can be modified by covalent attachment of a bioactive agent to a carboxylic group or amino group on the Peptide. The Peptides can be modified using any of a number of different coupling chemistries that covalently attach ligands to Peptides.

One useful protocol involves the "activation" of hydroxyl groups on the Peptide carbonyldiimidazole (CDI) in aprotic solvents such as DMSO, acetone, or THF. CDI forms an imidazolyl carbamate complex with the hydroxyl group which may be displaced by binding the free amino group of a bioactive ligand such as a protein. The reaction is an N-nucleophilic substitution and results in a stable N-alkylcarbamate linkage of the ligand to the Peptide. The resulting ligand-Peptide complex is stable and resists hydrolysis for extended periods of time.

Another coupling method involves the use of 1-ethyl-3-(3-dimethylaminopropyl) carbodiimide (EDAC) or "water-soluble CDI" in conjunction with N-hydroxylsulfosuccinimide (sulfo NHS) to couple the exposed carboxylic groups of the Peptide to the free amino groups of bioactive ligands. EDAC and sulfo-NHS form an activated ester with the carboxylic acid groups of the Peptide which react with the amine end of a ligand to form a Peptide bond. The resulting peptide bond is resistant to hydrolysis. The use of sulfo-NHS in the reaction increases the efficiency of the EDAC coupling by a factor of ten-fold and provides for exceptionally gentle conditions that ensure the viability of the ligand-Peptide complex. These protocols permit the activation of either hydroxyl or carboxyl groups on the Peptide, and attachment of the desired bioactive ligand.

A useful coupling procedure for attaching ligands with free hydroxyl and carboxyl groups to the Peptide involves the use of the cross-linking agent, divinylsulfone. This method is useful for attaching sugars or other hydroxylic compounds to hydroxyl groups on the Peptide. The activation involves the reaction of divinylsulfone with the hydroxyl groups of the Peptide to a vinylsulfonyl ethyl ether. The vinyl groups will couple to alcohols, phenols and amines. Activation and coupling take place at pH 11. The linkage is stable in the pH range from 1–8 and is suitable for transit through the intestine. Any suitable coupling method known to those skilled in the art may be used to couple bioactive ligands to the Peptide.

The bioactive agent can be covalently coupled to peptide either directly or indirectly using a linker molecule. Linker molecules will typically be used when additional flexibility or space is needed between the peptide and the therapeutic compound. Any suitable molecule that can be coupled to both protein and a bioactive agent can be used as a linked. Exemplary linkers are peptides or molecules with straight carbon chains.

Bioactive Agents

Any kind of bioactive agent can be attached to the Peptide using standard techniques. The resulting conjugate of the Peptide and the bioactive agent is referred to herein as a Peptide composition or a peptide-drug conjugate. The term biologically active material refers to a protein, carbohydrate, nucleic acid, lipid, organic compound such as a drug, or a combinations thereof, that causes a biological effect when administered in vivo to an animal including humans. As demonstrated by the data described above, the RNA pol II and CTD peptides have been demonstrated to deliver molecules as large as beta-galactosidase, as well as the Flag-epitope, to the nucleus.

Non-limiting examples of useful bioactive agents are proteins, polysaccharides, nucleic acids, nucleosides, nucleotides, minerals, inorganic compounds and organic compounds. The preferred bioactive agent is a nucleotide molecules such as a gene, cDNA, mRNA, antisense or ribozyme or external guide sequence for RNAase P. Genes for use in human gene transfer are reviewed, for example, by Anderson, *Science* 260, 808 (1992), Miller, *Nature* 357, 455 (1992), Mulligan, *Science* 260, 926 (1993), and Crystal, *Science* 270, 404 (1995). Ribozymes are reviewed, for example, by Sullenger and Cech, *Science* 262, 1566–1569 (1993), Barinaga, *Science* 262, 1512–1514 (1993), Yu, et al., *Proc. Natl. Acad. Sci. USA* 90, 6340–6344 (1993), and external guide sequences for targeted cleavage by ribonuclease P is described by Altman, *Proc. Natl. Acad. Sci. USA* 90(23), 10898–10900 (1993), Liu and Altman, *Genes & Devel.* 9(4), 471–480 (1995), Yuan, et al., *Proc. Natl. Acad. Sci. USA* 89(17), 8006–8010 (1992), and Altman, et al., *FASEB J.* 7(1), 7–14 (1993). Antisense oligonucleotides are described by Herrmann, *J. Molec. Med.* 73, 157–163 (1995), De Clercq, *Clin. Microbiol. Rev.* 8, 200–239 (1995), Wagner, *Nature* 372, 333–335 (1994), Crooke *Antisense Res. Develop.* 3, 1–2 (1993), Agrawal and Akhtar, *Trends in Biotechnol.* 13, 197–199 (1995), Agrawal, et al., *Clin. Pharmacokinetics* 28, 7–16 (1995), Agrawal, et al., *Current Opinion in Biotechnol.* 6, 9–12 (1995), Temsamani, et al., *Antisense Res. & Devel.* 4, 35–42 (1994), and Zamecnik, et al., *Nucleic Acids Symp. Series* 24, 127–131 (1991). The Peptides also can be used to deliver procaryotic and eucaryotic cells, e.g., bacteria, yeast, and mammalian cells, including human cells, and components thereof, such as cell walls, and conjugates of cellular components.

Peptide can also be used to deliver water soluble or water insoluble drugs such as anesthetics, chemotherapeutic agents, immunosuppressive agents, steroids, antibiotics, antivirals, antifungals, antiinflammatories, and anti-parasitic drugs.

Imaging agents also may be attached to Peptide, including metals, radioactive isotopes, radioopaque agents, fluorescent dyes, and radiolucent agents. Radioisotopes and radioopaque agents include gallium, technetium, indium, strontium, iodine, barium, and phosphorus.

Peptides Modified to Increase in vivo Half-lives

The peptides can be prepared by recombinant techniques and expression in an appropriate host systems, isolated from natural sources as described above, or prepared by synthetic means. These methods are known to those skilled in the art. An example is the solid phase synthesis described by J. Merrifield, 1964 *J. Am. Chem. Soc.* 85, 2149, used in U.S. Pat. No. 4,792,525, and described in U.S. Pat. No. 4,244,946, wherein a protected alpha-amino acid is coupled to a suitable resin, to initiate synthesis of a peptide starting from the C-terminus of the peptide. Other methods of synthesis are described in U.S. Pat. Nos. 4,305,872 and 4,316,891.

Peptides containing cyclopropyl amino acids, or amino acids derivatized in a similar fashion, can also be used. These peptides retain their original activity but have increased half-lives in vivo. Methods known for modifying amino acids, and their use, are known to those skilled in the art, for example, as described in U.S. Pat. No. 4,629,784 to Stammer.

The peptide can also be administered as a pharmaceutically acceptable acid- or base- addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

II. Exploiting the Targeting Properties of RNA Polymerase II's CTD to Concentrate Bioactive Agents at Sites of Transcription and Splicing.

The studies summarized above show that CTD peptides are versatile targeting modules, based on the following: they are phosphorylated efficiently in vivo; they are translocated into the nucleus without conventional nuclear localization signal; they are localized to discrete non-chromosomal domains and surrounding 'nucleoplasm'; they are redistributed from 'nucleoplasm' to discrete domains during states of transcriptional inhibition; they undergo a transcription-dependent the redistribution cycle similar to endogenous Pol II; they can induce global reorganization of ICGC (splicing) compartment in vivo; functionally redundant above effects do not require all CTD peptides; they have variable targeting/reorganizing properties depending upon the number of CTD heptapeptides; and they have variable targeting/reorganizing properties depending upon the composition of heptapeptides. The heptapeptides are sufficient to translocate a bioactive agent into the nucleus; target it to the sites where RNA pol II is localized or stored; and mediate a transcription dependent redistribution cycle, which is regulated by cellular kinases and phosphatases.

Therapeutic Applications

Since the CTD peptides accumulate precisely in discrete sites inhabited by RNA polymerase II and the spliceosomes, they should have significant applications in emerging genetic therapy technologies. CTD peptides may be attached to antisense oligonucleotides, catalytic RNAs and transgenes, as described above, to deliver and concentrate the nucleotide sequences in the nuclear compartment where the pre-mRNAs are synthesized and processed. The CTD peptides may minimize intranuclear sequestration of therapeutic polynucleotides.

In the preferred embodiment, the peptides are coupled to bioactive agent, then administered to a patient in need thereof. Those skilled in the art will know how much and in what formulation the peptide-drug conjugate is administered. Formulations for intravenous administration include saline and phosphate buffered solution as well as liposomes and other microparticulates which increase bioavailability and can be used for targeting to specific tissues; formulations for topical, transmucosal, and aerosol formulations are similarly available, for example, as described in Goodman and Gilmans. In some cases, the peptide-drug conjugates may be administerable orally, preferably in an enteric coating or microencapsulated to enhance uptake and bioavailability.

Modifications and variations of the present invention, isolated Pol II LS protein and Pol II LS antibodies, as well as methods of use thereof, will be obvious to those skilled in the art from the foregoing detailed description. Such modifications and variations are intended to come within the scope of the appended claims.

I claim:

1. A peptide construct comprising a peptide derived from the carboxyl terminal domain of RNA polymerase II comprising seven amino acid residues that shares the consensus sequence: $Y_1X_2P_3X_4X_5P_6X_7$ (SEQ ID NO. 21), wherein X is any amino acid and the peptide is not RNA polymerase II, wherein the peptide accumulates in discrete compartments within the nucleus of a cell in culture, having coupled thereto a bioactive agent deliverable to the nucleus of the cell, wherein the bioactive agent is active in the nucleus.

2. The peptide construct of claim 1 wherein X in the peptide is S or T.

3. The peptide construct of claim 1 wherein the peptide comprises a heptapeptide selected from the group consisting of the peptides set forth in SEQ ID NO. 1 through SEQ ID NO. 19.

4. The peptide construct of claim 1 wherein the peptide comprises the amino acid sequence Tyrosine—Serine—Proline—Threonine—Serine—Proline—Serine (SEQ ID NO. 1).

5. The peptide construct of claim 1 wherein the peptide is phosphorylated.

6. The peptide construct of claim 1 wherein more of the peptide construct accumulates in storage domains than in the diffuse nucleoplasm.

7. The peptide construct of claim 1 wherein the peptide redistributes to the Pol II genes and active splicing machinery.

8. The peptide construct of claim 1 wherein the peptide comprises multiple consensus repeats from a RNA polymerase II.

9. The peptide construct of claim 8 wherein the peptide further comprises variable repeats from a RNA polymerase II.

10. The peptide construct of claim 1 wherein the bioactive agent is a drug.

11. The peptide construct of claim 1 wherein the bioactive agent is selected from the group consisting of nucleosides, nucleotides, antisense, ribozymes, external guide sequences for RNAase P, genes, cDNA, and RNA.

12. A composition comprising a peptide construct comprising a peptide derived from the carboxyl terminal domain of RNA polymerase II comprising seven amino acid residues that shares the consensus sequence: $Y_1X_2P_3X_4X_5P_6X_7$ (SEQ ID NO. 21), wherein X is any amino acid and the peptide is not RNA polymerase II, wherein the peptide accumulates in discrete compartments within the nucleus of a cell in culture, having coupled thereto a bioactive agent deliverable to the nucleus of the cell, wherein the bioactive agent is active in the nucleus and is selected from the group consisting of nucleosides, nucleotides, antisense, ribozymes, external guide sequences for RNAase P, genes, cDNA, and RNA and a carrier for administration to cells in culture or isolated.

13. The peptide construct of claim 1 further comprising a detectable label.

14. A method for delivering a compound in vitro to the nucleus of a cell comprising administering to the cell a construct, the construct comprising a peptide derived from the carboxyl terminal domain of RNA polymerase II comprising seven amino acid residues that shares the consensus sequence: $Y_1X_2P_3X_4X_5P_6X_7$ (SEQ ID NO. 21), wherein X is any amino acid and the peptide is not RNA polymerase II, wherein the peptide accumulates in discrete compartments within the nucleus of a cell, coupled to the compound to be delivered, wherein the compound is deliverable into the nucleus and the compound is active in the nucleus.

15. The method of claim 14 wherein X in the peptide is S or T.

16. The method of claim 14 wherein the peptide comprises a heptapeptide selected from the group consisting of the peptides set forth in SEQ ID NO. 1 through SEQ ID NO. 19.

17. The method of claim 14 wherein the peptide comprises the amino acid sequence Tyrosine—Serine—Proline—Threonine—Serine—Proline—Serine (SEQ ID NO. 1).

18. The method of claim 14 wherein the peptide is phosphorylated.

19. The method of claim 14 wherein more of the peptide construct accumulates in storage domains than in the diffuse nucleoplasm.

20. The method of claim 14 wherein the peptide redistributes to the Pol II genes and active splicing machinery.

21. The method of claim 14 wherein the peptide further comprises multiple consensus repeats from a RNA polymerase II.

22. The method of claim 14 wherein the peptide further comprises variable repeats from a RNA polymerase II.

23. The method of claim 14 wherein the compound is a drug.

24. The method of claim 14 wherein the compound is selected from the group consisting of nucleosides, nucleotides, antisense, ribozymes, external guide sequences for RNAase P, genes, cDNA, and RNA.

25. The method of claim 24 further comprising administering the peptide to cells in cell culture.

26. The method of claim 14 wherein the peptide further comprises a detectable label, the method further comprising detecting the intranuclear location of the label after administration of the peptide to cells having a nucleus.

* * * * *